(12) United States Patent
Girlando et al.

(10) Patent No.: US 9,335,286 B2
(45) Date of Patent: May 10, 2016

(54) METHOD AND DEVICE FOR MONITORING AT LEAST A CHARACTERISTIC OF A BLOCK MADE OF A BUILDING MATERIAL

(71) Applicant: STMICROELECTRONICS S.R.L., Agrate Brianza (MB) (IT)

(72) Inventors: Giovanni Girlando, Catania (IT); Alessandro Finocchiaro, Catania (IT); Bruno Murari, Monza (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 753 days.

(21) Appl. No.: 13/770,492

(22) Filed: Feb. 19, 2013

(65) Prior Publication Data

US 2013/0221945 A1 Aug. 29, 2013

(30) Foreign Application Priority Data

Feb. 29, 2012 (IT) .............................. MI2012A0309

(51) Int. Cl.
*G01N 27/00* (2006.01)
*G01M 5/00* (2006.01)
*H04Q 9/00* (2006.01)

(52) U.S. Cl.
CPC ............. *G01N 27/00* (2013.01); *G01M 5/0083* (2013.01); *H04Q 9/00* (2013.01); *H04Q 2209/88* (2013.01)

(58) Field of Classification Search
CPC ..... G01N 27/00; H04Q 9/00; H04Q 2209/88; G01M 5/0083

USPC .......................................................... 324/71.1
See application file for complete search history.

(56) References Cited

U.S. PATENT DOCUMENTS

| 2004/0153270 A1 | 8/2004 | Yamashita et al. |
| 2005/0204825 A1 | 9/2005 | Kunerth et al. |
| 2012/0161789 A1 | 6/2012 | Girlando et al. |
| 2015/0253268 A1* | 9/2015 | Girlando ................ G01N 27/00 324/71.1 |

FOREIGN PATENT DOCUMENTS

| EP | 2469886 | 6/2012 |
| GB | 2426669 | 11/2006 |
| WO | 2012084295 | 6/2012 |

* cited by examiner

*Primary Examiner* — Thomas F Valone
(74) *Attorney, Agent, or Firm* — Allen, Dyer, Doppelt, Milbrath & Gilchrist, P.A.

(57) ABSTRACT

A monitoring device includes an electric supply line to be buried in the block of building material, to convey signals and to be AC supplied so as to generate voltage and current stationary waveforms. The device also includes primary inductors coupled to the electric supply line at positions corresponding to peaks of at least one of the voltage and current stationary waveforms. The device also includes integrated monitoring circuits to be buried in the block of building material, with each integrated monitoring circuit including an integrated sensor to sense at least one physical characteristic, and a secondary inductor magnetically coupled to a respective primary inductor to supply the integrated sensor, and communicate through the electric supply line.

20 Claims, 4 Drawing Sheets

METHOD AND DEVICE FOR MONITORING AT LEAST A CHARACTERISTIC OF A BLOCK MADE OF A BUILDING MATERIAL

FIELD OF THE INVENTION

This invention relates to monitoring devices for use in building structures, and, more particularly, to a method and a related monitoring device for at least one characteristic of a block of building material.

BACKGROUND

The strategy for implementing damage detection and the characterization of mechanical structures is commonly called Structural Health Monitoring (SHM). Damages are defined as modifications of the material and/or of the geometrical properties of a structural system, comprising modifications of boundary conditions and connections of the system, that worsen performance of the system. The SHM process implies the observation of the mechanical system over time using periodically: measurements of dynamic responses coming from an array of sensors, extraction of data of damage characteristics sensed from these measurements, and statistical analysis of these data of damage characteristics for determining the present health state of the system (also called structural analysis).

This process provides information about the capacity of the structure for carrying out its function, considering the unavoidable aging and degradation in working environments. After extreme events, such as earthquakes or explosions, the SHM is used for a quick screening of the conditions of the structure for providing, almost in real time, reliable information about the integrity of the structure itself.

Currently, SHM systems use sensors placed on the surfaces to be monitored. For example, sensors used (anemometers for calculating the wind speed, accelerometers, extensometers, motion transducers, temperature sensors, sensors for detecting motion of weights, etc.) for monitoring bridges are placed on the external surfaces of beams, ropes or pillars. This is done to: estimate the effects of loads on the bridge, evaluate the weakening of the bridge, and foresee the probable evolution of the bridge and its expected lifetime.

SHM systems with sensors to be buried in the building structure to be monitored have been devised. These sensors (pressure, humidity, temperature, etc.) have at least one remote powering and transmission antenna for transmitting the measured values outside of the block of building material. These kinds of sensors are disclosed, for example, in U.S. patent application No. 2004/0153270 and in Italian patent applications VA2010A000097 and MI2010A002365.

An inconvenience of the monitoring circuits to be buried in the building material includes the difficulties of powering them. In Italian patent application No. VA2010A000097, each monitoring circuit is powered through a magnetic coupling with an inductor connected to a shielded line, as shown in FIG. 1. In Italian patent application No. MI2010A002365 the monitoring circuits are fixed to a linear support, as shown in FIG. 2, and have remote powering antennas that receive the electromagnetic field irradiated by an external power supply.

SUMMARY OF THE INVENTION

In view of the foregoing background, it is therefore an object of the invention to provide a straightforward and efficient way of realizing a method and a related device for monitoring a block made of a building material, that allows powering of the monitoring circuits buried in the building material.

In the monitoring device according to the disclosed embodiments, it is not necessary to install a shielded line for each monitoring circuit nor to provide the monitoring circuits with a remote powering antenna, because the monitoring circuits have respective secondary windings of an internal power supply magnetically coupled to primary windings connected to a same electrical supply line at certain points.

By powering the AC electric line, an AC voltage and an AC current distributed as stationary waveforms are generated along the line, thus there are certain points, the location of which is known a priori, at which the amplitude of the voltage or of the current assumes a relative maximum. The primary inductors of the monitoring device are conveniently connected to the line near or exactly at these points, such as to be crossed by an AC current and to generate a magnetic field. Each integrated monitoring circuit may have a secondary inductor magnetically coupled to a respective primary inductor, such as to provide an internal supply voltage for the circuit. Moreover, the secondary inductor may advantageously resonate at the working frequency with the equivalent input capacitance of the integrated circuit.

The inductors may be connected in series in the electric line in correspondence with the peaks of the current stationary waveform, or be connected electrically in parallel with the electric line in correspondence with the peaks of the voltage stationary waveform.

According to an embodiment, the electric line is equipped, in correspondence with a terminal end, with an antenna for remote powering and for data transmission.

DESCRIPTION OF EXEMPLARY EMBODIMENTS

Figure 1:
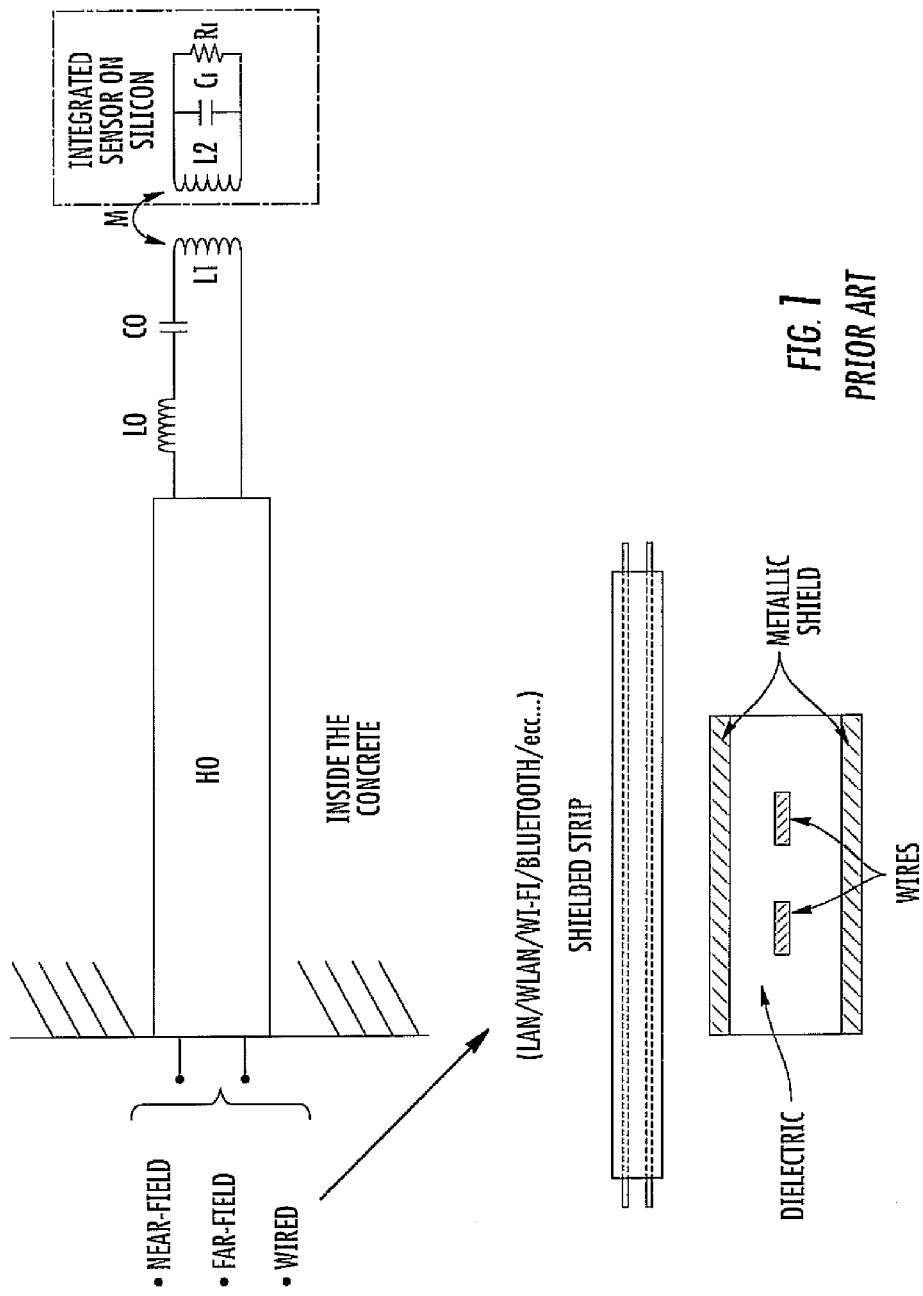
FIG. 1 is a schematic diagram of a shielded line that powers a monitoring circuit buried in a building material, disclosed in Italian patent application No. VA2010A000097, as in the prior art.
Figure 2:
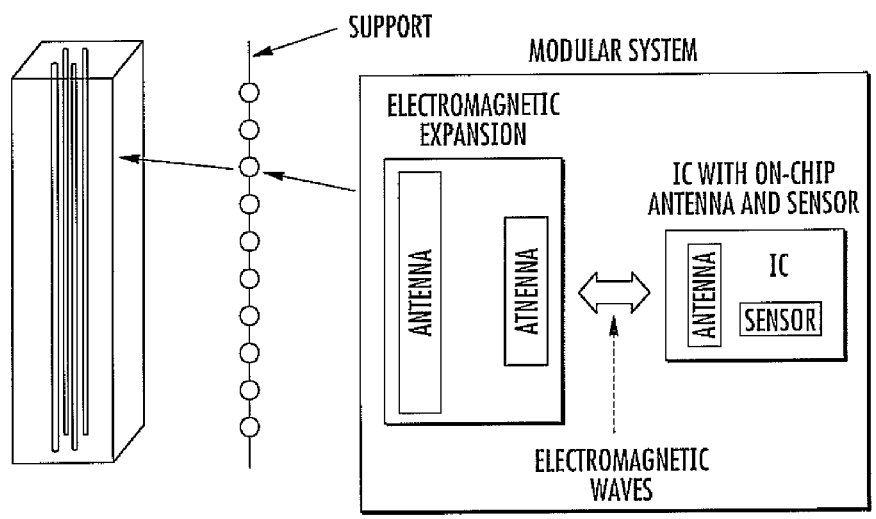
FIG. 2 is a schematic diagram depicting monitoring circuits connected to a same linear support and buried in a building material, disclosed in Italian patent application No. MI2010A002365, as in the prior art.
Figure 3:
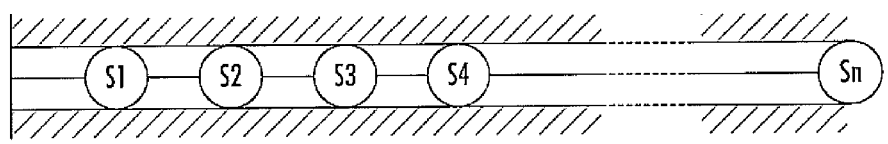
FIG. 3 is a schematic diagram depicting a monitoring device of the invention embedded in a block of building material having a plurality of buried monitoring circuits coupled to a same electric line.

An embodiment of a monitoring device of this invention is schematically shown in FIG. 3. The monitoring device that is depicted when buried inside a block of building material, has an electrical supply line to which monitoring circuits S1, S2, ... Sn are functionally coupled. These monitoring circuits have sensors capable of sensing at least one physical characteristic of the building material in which they are buried, and secondary inductors L2 of the internal power supply.

When the electric line is AC powered, stationary voltage and current waveforms are generated by the superposition of a progressive wave and of a reflected wave. In the field of transmission lines it is well known that this effect is maximum in electric lines that end with a short-circuit (null impedance) or with an open circuit (infinite impedance), because in these cases the electric line does not absorb active power, but only reactive power. If the lines were connected with a non-null finite impedance at their end, the above described phenomenon would still occur, but would be attenuated.

Figure 4:
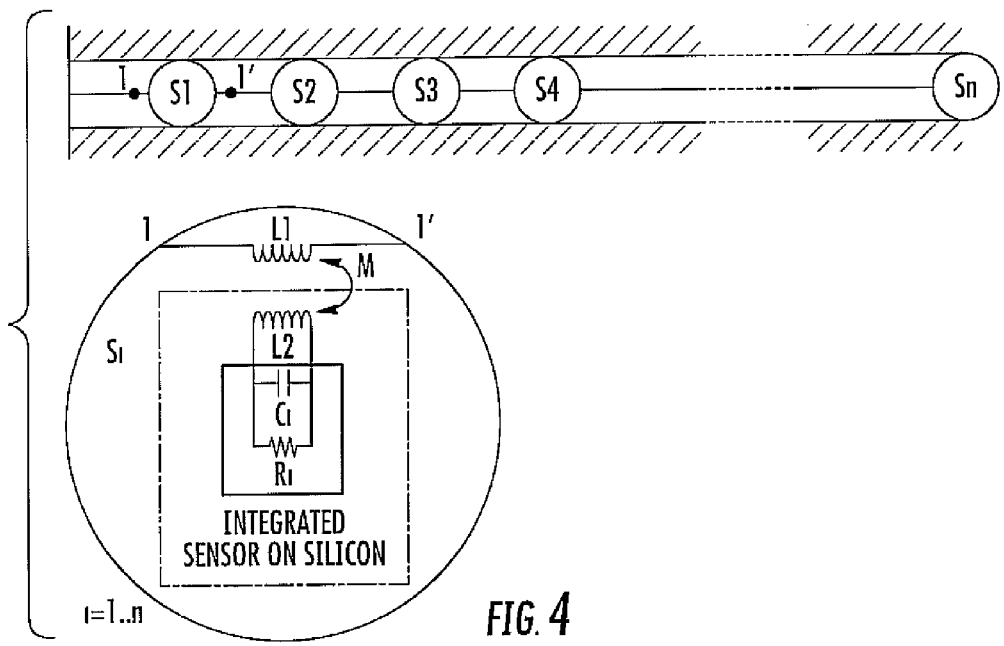
FIG. 4 is a schematic diagram illustrating a magnetic coupling between a monitoring circuit, schematically represented with its input impedance, and a respective series inductor of the electric line as in the present invention.

As shown in FIG. 4, the device has primary inductors L1 disposed along the electrical power supply line in correspondence with the peaks of voltage and/or current stationary waveforms, such as to be crossed by current. The monitoring circuits S1, ... S2, Sn have secondary inductors L2 magnetically coupled to respective primary inductors L1, such as to generate on its nodes an induced supply voltage of the respective circuit. Moreover, to maximize this induced supply voltage, the secondary inductors L2 may be realized such as to resonate at the working frequency with the equivalent input capacitances of the integrated circuit. By realizing in this way the monitoring device, all of its sensors may be supplied through a single electric line and without using remote powering antennas integrated in the monitoring circuits.

Figure 5:
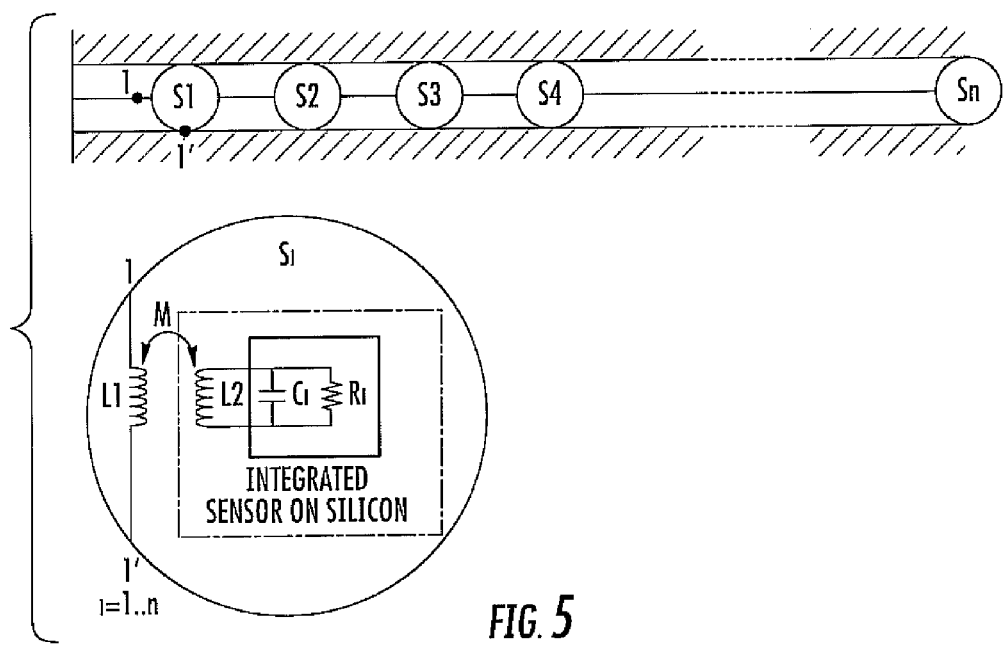
FIG. 5 is a schematic diagram illustrating a magnetic coupling between a monitoring circuit and a respective parallel inductor connected between the forward path and the return path of the electric line as in the present invention.

The embodiment of FIG. 5 is similar to that of FIG. 4, though in this case the primary inductors L1 are placed in correspondence with the peaks of the voltage stationary waveform and are connected in parallel with the electric supply line. Between the points 1 and 1' there is an AC voltage having an amplitude equal to the corresponding peak of the stationary waveform, thus the primary inductor L1 is crossed by an AC current that will allow powering of the corresponding monitoring circuit because of the magnetic coupling with the related secondary inductor L2.

Figure 6:
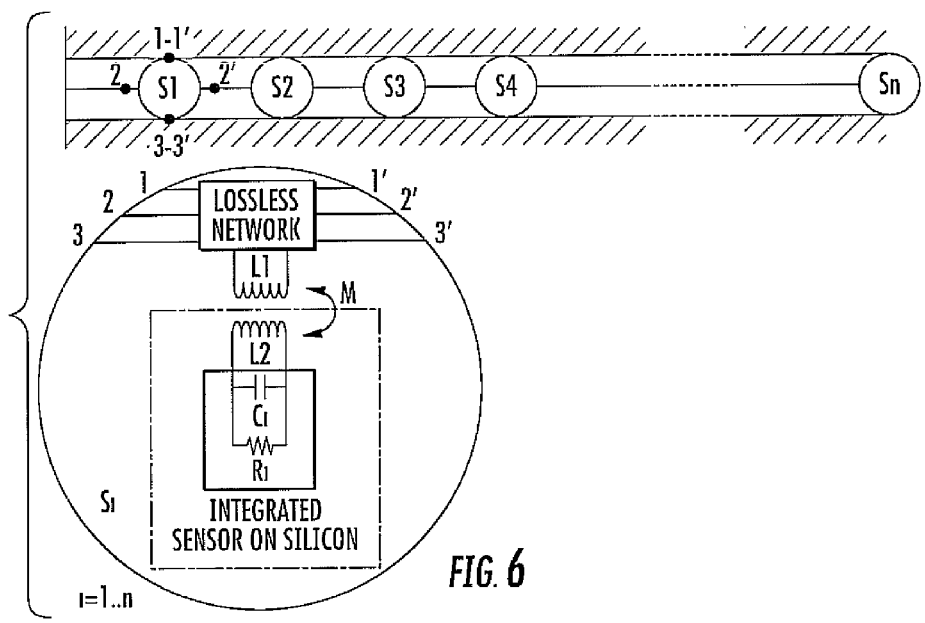
FIG. 6 is a schematic diagram showing a matching network connected to the buried electric line as in the present invention.

According to yet another embodiment depicted in FIG. 6, the electric supply line is equipped with lossless impedance matching networks placed in correspondence with the peaks of voltage and/or current stationary waveforms that resonate at the working frequency with the respective primary inductor L1. The working principle is the same as that discussed referring to FIGS. 4 and 5.

According to a method aspect, once the monitoring device is placed inside the structure to be monitored, the electric line is AC powered. Thus voltage and current stationary waveforms are generated with peaks located in correspondence with the primary inductors L1, that will power the sensors buried in the building material. The signals generated by the sensors and transmitted through the electric line are received, by using the magnetic coupling between the secondary inductors L2 and the respective primary inductors L1.

Furthermore, it is possible to realize blocks made of a building material embedding the monitoring devices described herein.

Figure 7:
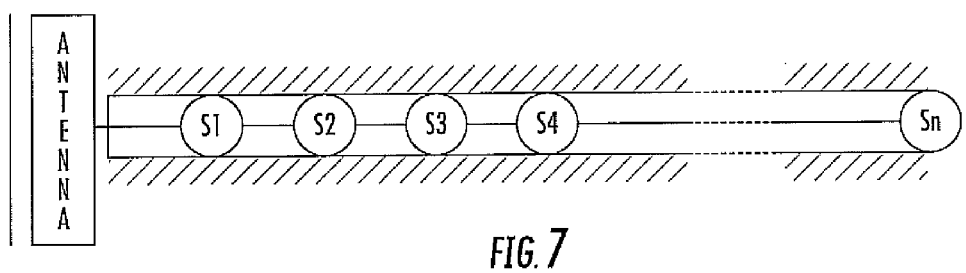
FIG. 7 is a schematic diagram showing a monitoring device of this invention embedded in a block of building material having a plurality of buried monitoring circuits coupled to a same electric line ending with a buried antenna for remote powering and for data transmission.

Advantageously but not necessarily, the electric line ends with a remote powering and data transmission antenna buried in the block of building material, as schematically shown in FIG. 7.

The invention claimed is:

1. A monitoring device for at least one physical characteristic of a block of building material, comprising:
   an electric supply line configured to be buried in the block of building material, to convey signals and to be AC supplied so as to generate voltage and current stationary waveforms;
   a plurality of primary inductors operatively coupled to the electric supply line at positions corresponding to peaks of at least one of the voltage and current stationary waveforms when the electric supply line is AC powered;
   a plurality of integrated monitoring circuits configured to be buried in the block of building material, each integrated monitoring circuit comprising
      an integrated sensor configured to sense the at least one physical characteristic, and
      a secondary inductor magnetically coupled to a respective one of the plurality of primary inductors and configured to supply the integrated sensor, and communicate through the electric supply line.

2. The monitoring device of claim 1, further comprising an antenna coupled to the electric supply line configured to be remotely powered and transmit sensed values of the at least one physical characteristic.

3. The monitoring device of claim 1, wherein at least one of the primary inductors is electrically connected in series with the electric supply line in correspondence with peaks of the current stationary waveform.

4. The monitoring device of claim 1, wherein at least one of the primary inductors is electrically connected in parallel with the electric supply line in correspondence with peaks of the voltage stationary waveform.

5. The monitoring device of claim 1, further comprising a resonant network coupled to at least one of the primary inductors.

6. A monitoring device for a block of building material, comprising:
   an electric supply line configured to be buried in the block of building material;
   a plurality of primary inductors coupled to the electric supply line at positions based upon peaks of at least one stationary waveform when the electric supply line is AC powered;
   a plurality of integrated monitoring circuits configured to be buried in the block of building material, each integrated monitoring circuit comprising
      an integrated sensor, and
      a secondary inductor magnetically coupled to a respective one of the primary inductors and configured to supply the integrated sensor, and communicate through the electric supply line.

7. The monitoring device of claim 6, further comprising an antenna coupled to the electric supply line configured to be remotely powered and transmit sensed values of the at least one physical characteristic.

8. The monitoring device of claim 6, wherein at least one of the primary inductors is electrically connected in series with the electric supply line in correspondence with peaks of a current stationary waveform.

9. The monitoring device of claim 6, wherein at least one of the primary inductors is electrically connected in parallel with the electric supply line in correspondence with peaks of a voltage stationary waveform.

10. The monitoring device of claim 6, further comprising a resonant network coupled to at least one of the primary inductors.

11. A monitoring device comprising:
    a block of building material;
    an electric supply line buried in the block of building material;

a plurality of primary inductors coupled to the electric supply line at positions based upon peaks of at least one stationary waveform when the electric supply line is AC powered;

a plurality of integrated monitoring circuits buried in the block of building material, each integrated monitoring circuit comprising an integrated sensor, and a secondary inductor magnetically coupled to a respective one of the primary inductors and configured to supply the integrated sensor, and communicate through the electric supply line.

12. The monitoring device of claim 11, further comprising an antenna coupled to the electric supply line configured to be remotely powered and transmit sensed values of the at least one physical characteristic.

13. The monitoring device of claim 11, wherein at least one of the primary inductors is electrically connected in series with the electric supply line in correspondence with peaks of a current stationary waveform.

14. The monitoring device of claim 11, wherein at least one of the primary inductors is electrically connected in parallel with the electric supply line in correspondence with peaks of a voltage stationary waveform.

15. The monitoring device of claim 11, further comprising a resonant network coupled to at least one of the primary inductors.

16. A method of sensing at least one physical characteristic using a monitoring device comprising an electric supply line buried in a block of building material, a plurality of primary inductors coupled to the electric supply line at positions based upon peaks of at least one stationary waveform when the electric supply line is AC powered, and a plurality of integrated monitoring circuits buried in the block of building material and comprising a secondary inductor magnetically coupled to a respective one of the primary inductors, the method comprising:

powering the electric supply line with AC at a frequency generating the at least one stationary waveform and thereby powering each integrated monitoring circuit via a respective primary and secondary inductor; and receive sensed signals related to at least one physical characteristic from each integrated monitoring circuit via the electric supply line.

17. The method of claim 16, wherein the monitoring device further comprises an antenna coupled to the electric supply line.

18. The method of claim 16, wherein at least one of the primary inductors is electrically connected in series with the electric supply line in correspondence with peaks of a current stationary waveform.

19. The method of claim 16, wherein at least one of the primary inductors is electrically connected in parallel with the electric supply line in correspondence with peaks of a voltage stationary waveform.

20. The method of claim 16, wherein the monitoring device further comprises a resonant network coupled to at least one of the primary inductors.

* * * * *